US009446016B2

(12) United States Patent
Hughes et al.

(10) Patent No.: US 9,446,016 B2
(45) Date of Patent: Sep. 20, 2016

(54) METHODS OF TREATING AGE RELATED DISORDERS

(71) Applicant: Zafgen, Inc., Cambridge, MA (US)

(72) Inventors: Thomas E. Hughes, Boston, MA (US); James E. Vath, Lynnfield, MA (US)

(73) Assignee: Zafgen, Inc., Boston, MA (US)

( * ) Notice: Subject to any disclaimer, the term of this patent is extended or adjusted under 35 U.S.C. 154(b) by 73 days.

(21) Appl. No.: 14/244,278

(22) Filed: Apr. 3, 2014

(65) Prior Publication Data
US 2014/0336251 A1    Nov. 13, 2014

Related U.S. Application Data

(63) Continuation of application No. PCT/US2012/000461, filed on Oct. 3, 2012.

(60) Provisional application No. 61/542,393, filed on Oct. 3, 2011.

(51) Int. Cl.
*A61K 31/335* (2006.01)
*C07D 303/08* (2006.01)
*C07D 303/12* (2006.01)
*A61K 31/336* (2006.01)
*A61K 31/7088* (2006.01)
*A61K 31/713* (2006.01)
*C07D 303/18* (2006.01)

(52) U.S. Cl.
CPC .......... *A61K 31/336* (2013.01); *A61K 31/335* (2013.01); *A61K 31/7088* (2013.01); *A61K 31/713* (2013.01); *C07D 303/08* (2013.01); *C07D 303/12* (2013.01); *C07D 303/18* (2013.01)

(58) Field of Classification Search
CPC . A61K 31/335; C07D 303/08; C07D 303/12
See application file for complete search history.

(56) References Cited

U.S. PATENT DOCUMENTS

| | | | |
|---|---|---|---|
| 5,164,410 A | 11/1992 | Kishimoto et al. | |
| 5,166,172 A | 11/1992 | Kishimoto et al. | |
| 5,180,735 A | 1/1993 | Kishimoto et al. | |
| 5,180,738 A | 1/1993 | Kishimoto et al. | |
| 5,196,406 A | 3/1993 | Kamei et al. | |
| 5,204,345 A | 4/1993 | Kishimoto et al. | |
| 5,288,722 A | 2/1994 | Kishimoto et al. | |
| 5,290,807 A | 3/1994 | Folkman et al. | |
| 5,422,363 A | 6/1995 | Yanai et al. | |
| 5,536,623 A | 7/1996 | Ohmachi et al. | |
| 5,698,586 A | 12/1997 | Kishimoto et al. | |
| 5,767,293 A | 6/1998 | Oku et al. | |
| 5,846,562 A | 12/1998 | Yanai et al. | |
| 5,900,431 A | 5/1999 | Molina et al. | |
| 6,017,949 A | 1/2000 | D'Amato et al. | |
| 6,017,954 A | 1/2000 | Folkman et al. | |
| 6,040,337 A | 3/2000 | Hong, II et al. | |
| 6,063,812 A | 5/2000 | Hong et al. | |
| 6,180,626 B1 | 1/2001 | Shimomura et al. | |
| 6,207,704 B1 | 3/2001 | Liu et al. | |
| 6,242,494 B1 | 6/2001 | Craig et al. | |
| 6,277,391 B1 | 8/2001 | Seo et al. | |
| 6,306,819 B1 | 10/2001 | Rupnick et al. | |
| 6,323,228 B1 | 11/2001 | BaMaung et al. | |
| 6,383,471 B1 | 5/2002 | Chen et al. | |
| 6,548,477 B1 | 4/2003 | Olson et al. | |
| 6,566,541 B2 | 5/2003 | Liu et al. | |
| 6,664,244 B1 | 12/2003 | Furuse et al. | |
| 6,803,382 B2 | 10/2004 | Eustache et al. | |
| 6,877,863 B2 | 4/2005 | Wood et al. | |
| 6,989,392 B2 | 1/2006 | Collins et al. | |
| 7,030,262 B2 | 4/2006 | BaMaung et al. | |
| 7,037,890 B2 | 5/2006 | Olson et al. | |
| 7,084,108 B2 | 8/2006 | Olson et al. | |
| 7,268,111 B2 | 9/2007 | Olson et al. | |
| 7,304,082 B2 | 12/2007 | Marino, Jr. et al. | |
| 7,718,695 B2 | 5/2010 | Kim et al. | |
| 8,367,721 B2 | 2/2013 | Hughes et al. | |
| 8,642,650 B2 | 2/2014 | Hughes et al. | |
| 8,980,946 B2 | 3/2015 | Hughes | |
| 9,000,035 B2 | 4/2015 | Hughes | |
| 9,173,865 B2 | 11/2015 | Hughes | |
| 2002/0002152 A1 | 1/2002 | Craig et al. | |
| 2003/0220371 A1 | 11/2003 | Kallander et al. | |
| 2004/0067266 A1 | 4/2004 | Toppo | |
| 2004/0116490 A1 | 6/2004 | Marino, Jr. et al. | |
| 2004/0116495 A1 | 6/2004 | Marino, Jr. et al. | |

(Continued)

FOREIGN PATENT DOCUMENTS

EP          0682020 A1    11/1995
WO    WO-98/56372 A1    12/1998

(Continued)

OTHER PUBLICATIONS

Anderson, "The Use of Fumagillin in Amoebiasis," Ann N Y Acad Sci., 55(6):1118-1124 (1952).

Benny et al., "An Orally Delivered Small-Molecule Formulation with Antiangiogenic and Anticancer Activity," Nat Biotechnol. Jul. 2008;26(7):799-807.

Bernier et al., "Fumagillin class inhibitors of methionine aminopeptidase-2," Drugs of the Future 30(5): 497-500 (2005).

Brakenhielm et al., "Angiogenesis Inhibitor, TNP-470, Prevents Diet-Induced and Genetic Obesity in Mice", Circulation Research, http://circres.ahajournals.org (accessed on Feb. 8, 2007).

(Continued)

Primary Examiner — Yong Chong
(74) Attorney, Agent, or Firm — Goodwin Procter LLP

(57) ABSTRACT

The invention generally relates to methods of treating a patient having, and/or at risk of, oxidative distress disorders and/or age-related disorders. The disclosure also generally relates to methods of treating memory impairment or enhancing the cognitive function of a patient in need thereof. Such methods may include administering a therapeutically effective amount of a MetAP2 inhibitor.

10 Claims, 3 Drawing Sheets

(56) References Cited

U.S. PATENT DOCUMENTS

| | | |
|---|---|---|
| 2004/0157836 A1 | 8/2004 | Comess et al. |
| 2004/0167128 A1 | 8/2004 | Comess et al. |
| 2004/0192914 A1 | 9/2004 | Kallander et al. |
| 2004/0204472 A1 | 10/2004 | Briggs et al. |
| 2005/0004116 A1 | 1/2005 | Kallander et al. |
| 2005/0037994 A1 | 2/2005 | Kim et al. |
| 2005/0113420 A1 | 5/2005 | Nan et al. |
| 2005/0239878 A1 | 10/2005 | Thompson et al. |
| 2006/0045865 A1 | 3/2006 | Jacob et al. |
| 2006/0069161 A1 | 3/2006 | Lee et al. |
| 2006/0276512 A1 | 12/2006 | Han et al. |
| 2007/0078172 A1 | 4/2007 | McElroy et al. |
| 2008/0200402 A1 | 8/2008 | Alvinerie et al. |
| 2009/0148396 A1 | 6/2009 | Akullian et al. |
| 2010/0016425 A1 | 1/2010 | Vath |
| 2010/0111894 A1 | 5/2010 | Benny-Ratsaby et al. |
| 2012/0004162 A1 | 1/2012 | Vath |
| 2012/0010259 A1 | 1/2012 | Vath |
| 2012/0010290 A1 | 1/2012 | Vath |
| 2012/0034233 A1 | 2/2012 | Hughes et al. |
| 2012/0322867 A1 | 12/2012 | Hughes et al. |
| 2014/0045934 A1 | 2/2014 | Hughes |
| 2014/0045935 A1 | 2/2014 | Hughes |
| 2014/0051752 A1 | 2/2014 | Hughes |
| 2015/0150840 A1 | 6/2015 | Vath |
| 2015/0209320 A1 | 7/2015 | Hughes et al. |
| 2015/0209321 A1 | 7/2015 | Hughes |
| 2015/0335608 A1 | 11/2015 | Hughes et al. |

FOREIGN PATENT DOCUMENTS

| | | |
|---|---|---|
| WO | WO-99/39702 A2 | 8/1999 |
| WO | WO-99/057097 A2 | 11/1999 |
| WO | WO-99/59986 A1 | 11/1999 |
| WO | WO-99/59987 A1 | 11/1999 |
| WO | WO-00/64876 A1 | 11/2000 |
| WO | WO-02/26782 A2 | 4/2002 |
| WO | WO-02/42295 A2 | 5/2002 |
| WO | WO-02/083065 A2 | 10/2002 |
| WO | WO-03/027104 A1 | 4/2003 |
| WO | WO-03/082845 A1 | 10/2003 |
| WO | WO-2004/033419 A1 | 4/2004 |
| WO | WO-2005/066197 A2 | 7/2005 |
| WO | WO-2005/082349 A1 | 9/2005 |
| WO | WO-2006/010498 A2 | 2/2006 |
| WO | WO-2006/080591 A1 | 8/2006 |
| WO | WO-2009/073445 A2 | 6/2009 |
| WO | WO-2010/042163 A2 | 4/2010 |
| WO | WO-2010/048499 A1 | 4/2010 |
| WO | WO-2010/065877 A2 | 6/2010 |
| WO | WO-2010/065879 A2 | 6/2010 |
| WO | WO-2010/065881 A2 | 6/2010 |
| WO | WO-2010/065883 A2 | 6/2010 |
| WO | WO-2011/044506 A2 | 4/2011 |
| WO | WO-2011/085198 A1 | 7/2011 |
| WO | WO-2011/085201 A1 | 7/2011 |
| WO | WO-2011/088055 A2 | 7/2011 |
| WO | WO-2011/127304 A2 | 10/2011 |
| WO | WO-2011/150338 A1 | 12/2011 |
| WO | WO-2012/012642 A1 | 1/2012 |
| WO | WO-2012/064838 A1 | 3/2012 |
| WO | WO-2012/051318 A1 | 4/2012 |
| WO | WO-2012/064928 A1 | 5/2012 |
| WO | WO-2012/074968 A1 | 6/2012 |
| WO | WO-2012/075020 A1 | 6/2012 |
| WO | WO-2012/075026 A1 | 6/2012 |
| WO | WO-2012/103333 A1 | 8/2012 |
| WO | WO-2012/122264 A1 | 9/2012 |
| WO | WO-2012/154676 A1 | 11/2012 |
| WO | WO-2012/154678 A1 | 11/2012 |
| WO | WO-2012/154679 A1 | 11/2012 |
| WO | WO-2013/033430 A1 | 3/2013 |
| WO | WO-2013/055385 A2 | 4/2013 |
| WO | WO-2013/109735 A1 | 7/2013 |
| WO | WO-2013/109739 A1 | 7/2013 |
| WO | WO-2013/169727 A1 | 11/2013 |
| WO | WO-2013/169857 A1 | 11/2013 |
| WO | WO-2013/169860 A1 | 11/2013 |

OTHER PUBLICATIONS

Braunwald et al., "Obesity" in Harrison's Principles of Internal Medicine, 15th Ed., McGraw Hill (New York) pp. 479-486 (2001).

Chun et al., "Novel inhibitors targeted to methionine aminopeptidase 2 (MetAP2) strongly inhibit the growth of cancers in xenografted nude model," Int. J. Cancer 114(1):124-30 (2005).

Didier et al., "Antimicrosporidial Activities of Fumagillin, TNP-470, Ovalicin, and Ovalicin Derivatives in Vitro and In Vivo", Antimicrob Agents Chemother. Jun;50(6):2146-55 (2006).

DiPaolo et al., "Studies on the Carcinolytic Activity of Fumagillin and Some of its Derivatives," Antibiot Annu.:6:541-546 (1958-1959).

Drevs et al., "Antiangiogenic Potency of FK866/K22.175, a New Inhibitor of Intracellular NAD Biosynthesis, In Murine Renal Cell Carcinoma", Anticancer Res. Nov.-Dec.;23(6C):4853-4858 (2003).

Dumas et al., "Synthesis and Structure Activity Relationships of Novel Small Molecule Cathepsin D Inhibitors," Bioorg Med Chem Lett.Sep. 6;9(17):2531-2536 (1999).

Eder et al., "Phase 1 Dose Escalation Safety & Tolerance Study of PPI-2458 in Subjects with Non-Hodgkin's Lymphoma or Solid Tumors", (Presented on Nov. 7-10, 2006 at EORTC-NCIAACR Symposium on "Molecular Targets and Cancer Therapeutics.").

European Search Report for EP 09798793 dated Oct. 11, 2011, 9 pages.

Evdokimov et al., "Serendipitous discovery of novel bacterial methionine aminopeptidase inhibitors," Proteins Feb. 15;66(3):538-546 (2007).

Everhart "Contributions of Obesity and Weight Loss to Gallstone Disease," Ann Intern Med. Nov. 15:119(10):1029-1035 (1993).

Garrabrant et al., "Small molecule inhibitors of methionine aminopeptidase type 2 (MetAP-2) fail to inhibit endothelial cell proliferation or formation of microvessels from rat aortic rings in vitro," Angiogenesis, 7(2):91-96 (2004).

Garrison et al., "A metabolic basis for fibromyalgia and its related disorders: the possible role of resistance to thyroid hormone" Med Hypotheses. Aug;61(2):182-189 (2003).

Han et al., "Design and Synthesis of Highly Potent Fumagillin Analogues from Homology Modeling for a Human MetAP-2," Bioorg Med Chem Lett. Jan. 3;10(1):39-43 (2000).

Huang et al., "Inhibition of monometalated methionine aminopeptidase: inhibitor discovery and crystallographic analysis," J. Med. Chem., Nov. 15;50(23):5735-42. Epub Oct. 19, 2007 (2007).

Ingber et al., "Synthetic analogues of fumagillin that inhibit angiogenesis and suppress tumour growth," Nature, 348(6301):555-557 (Dec. 6, 1990).

International Search Report for International Application No. PCT/US2010/052050, International Filing Date Mar. 2, 2011, 4 pages.

International Search Report for International Application No. PCT/US2011/020515, International Filing Date Jul. 1, 2011 (4 pages).

International Search Report for International Application No. PCT/US2011/020866, mailed Jul. 22, 2011, 8 pages.

International Search Report for International Application No. PCT/US2011/060127, mailed Jan. 2, 2012, 2 pages.

International Search Report for International Application No. PCT/US2011/062320, mailed Feb. 17, 2012, 3 pages.

International Search Report for International Application No. PCT/US2011/38352, International Filing Date May 27, 2011 (3 pages).

International Search Report for International Application No. PCT/US2012/000461, mailed May 2, 2013, 7 pages.

International Search Report for International Application No. PCT/US2011/062421, mailed Feb. 17, 2012, 3 pages.

Jeong et al, "Total Synthesis and Antiangiogenic Activity of Cyclopentane Analogues of Fumagillol", Bioorg Med Chem Lett., Aug. 1;15(15):3580-3583 (2005).

Kawai et al., "Development of sulfonamide compounds as potent methionine aminopeptidase type II inhibitors with antiproliferative properties", Bioorg Med Chem Lett. Jul. 1, 2006;16(13):3574-7. Epub May 2, 2006.

(56) References Cited

OTHER PUBLICATIONS

Kim et al. "Assessment of the Anti-Obesity Effects of the TNP-470 Analog, CKD-732", J Mol Endocrinol. Apr;38(4):455-465 (2007).
Kim et al. "Depletion of methionine aminopeptidase 2 does not alter cell response to fumagillin or bengamides", Cancer Res. May 1;64(9):2984-2987 (2004).
Kim et al., "Development of parenteral formulation for a novel angiogenesis inhibitor, CKD-732 through complexation with hydroxypropyl-beta-cyclodextrin", Int J Pharm. Mar. 19;272(1-2):79-89 (2004).
Kim et al., "General pharmacology of CKD-732, a new anticancer agent: effects on central nervous, cardiovascular, and respiratory system," Biol Pharm Bull. Feb;28(2):217-223 (2005).
Kruger, Erwin A., "TNP-470: An Angiogenesis Inhibitor in Clinical Development for Cancer," Expert Opin Investig Drugs. Jun;9(6):1383-1396 (2003).
Lee et al., "Absorption, distribution, metabolism, and excretion of CKD-732, a novel antiangiogenic fumagillin derivative, in rats, mice, and dogs," Arch Pharm Res., Feb;27(2):265-72 (2004).
Lee et al., "Design, Synthesis, and Antiangiogenic Effects of a Series of Potent Novel Fumagillin Analogues," Chem Pharm Bull (Tokyo). Jul;55(7):1024-1029 (2007).
Lee et al., "Selective N-demethylation of tertiary aminofumagillols with selenium dioxide via a non-classical Polonovski type reaction," Heterocycles 68(5):915-932 (2006).
Lijnen et al., "Fumagillin Reduces Adipose Tissue Formation in Murine Models of Nutritionally Induced Obesity," Obesity (Silver Spring). Dec. 2010;18(12):2241-6. doi: 10.1038/oby.2009.503. Epub Jan. 21, 2010.
Luo et al., "Discovery and Structural Modification of Inhibitors of Methionine Aminopeptidases from *Escherichia coli* and *Saccharomyces cerevisiae*," J. Med. Chem. Jun. 19;46(13):2631-2640 (2003).
Ma et al., "Structural analysis of inhibition of *E. coli* methionine aminopeptidase: implication of loop adaptability in selective inhibition of bacterial enzymes," BMC Struct Biol., Dec. 19;7:84 (2007).
Masiero et al., "New Anti-angiogenesis Agents: Review of the Clinical Experience with Carboxyamido-Triazole (CAI), Thalidomide, TNP-470 and Interleukin-12", Angiogenesis, 1(1):23-35 (1997).
McCowan et al., "Fumagillin (H-3), a New Antibiotic with Amebicidal Properties", Science, 113(2930):202-203 (Feb. 23, 1951).
Milkowski et al., "TNP-470," Antiangiogenic Agents in Cancer Therapy, Chapter 22, pp. 385-398 (2012).
Molina et al. "Fumagillin Treatment of Intestinal Microsporidiosis," N. Engl. J. Med., 346(25):1963-1969 (Jun. 20, 2002).
Molina et al., "Potential Efficacy of Fumagillin in Intestinal Microsporidiosis Due to Enterocytozoon Bieneusi in Patients with HIV Infection: Results of a Drug Screening Study", AIDS (13):1603-1610 (Nov. 11, 1997).
Molina et al., "Trial of Oral Fumagillin for the Treatment of Intestinal Microsporidiosis in Patients with HIV Infection," AIDS;14(10):1341-1348 (Jul. 7, 2000).
Mosteller "Simplified calculation of body-surface area," N Engl J Med., 317(17):1098 (Oct. 22, 1987).
Myung et al. "The identification of in vitro metabolites of CKD-732 by liquid chromatography/tandem mass spectrometry", Rapid Commun Mass Spectrom. 2002;16(21):2048-53.
Naganuma et al. "Metronomic Doxifluridine Chemotherapy Combined with the Anti-Angiogenic Agent TNP=470 Inhibits the Growth of Human Uterine Carcinosarcoma Xenografts," Cancer Sci. Aug. 2011;102(8):1545-52.
National Task Force on the Prevention and Treatment of Obesity "Very Low-Calorie Diets", JAMA 270(8):967-974 (1993).
Noel et al., "Increased Risk of Acute Pancreatitis and Biliary Disease Observed in Patients with Type 2 Diabetes," Diabetes Care. May 2009;32(5):834-8. doi: 10.2337/dc08-1755. Epub Feb. 10, 2009.
Pagliarulo et al., "Gallstone disease and related risk factors in a large cohort of diabetic patients," Dig Liver Dis. Feb. 2004;36(2):130-134.
Picoul et al., "Progress in fumagillin synthesis," Pure Appl. Chem., 75:(2-3) pp. 235-249 (2003).
Rupnick, MA., "Adipose Tissue Mass Can be Regulated Through the Vasculature," Proc. Natl. Acad. Sci. USA:99(16):10730-10735 (2002).
Seneca et al., "Amebiasis: a review. II. Laboratory diagnosis, differential diagnosis and therapy," Am. J. Dig. Dis.,1(7):310-322 (1956).
Sheppard et al. "3-Amino-2-hydroxyamides and related compounds as inhibitors of methionine aminopeptidase-2", Bioorg Med Chem Lett. Feb. 23, 2004;14(4):865-8.
Shin et al., "A Phase Ib Pharmacokinetic study of the anti-angiogenic agent CKD-732 used in combination with capecitabine and oxaliplatin (XELOX) in metastatic colorectal cancer patients who progressed on irinotecan-based chemotherapy," Invest New Drugs, 30(2):672-680 (2012).
Shin, "A Phase I Pharmacokinetic and Pharmacodynamic Stdy of CKD-732, an Antiangiogenic Agent, in Patients with Refractory Solid Cancer", Invest New Drugs 28:650-658, (2010) Published online Dec. 29, 2010.
Srikumar et al. "Structural insights on Brugia malayi transglutaminase with cinnamoyl derivatives—a molecular docking approach", International Journal of Pharma and Bio Sciences 3(3):998-1006, 2012.
Towbin et al., "Proteomics-based target identification: bengamides as a new class of methionine aminopeptidase inhibitors," J. Biol. Chem. 278(52):52964-52971 (2003).
Vedantham et al., "Studies towards the synthesis of methionine aminopeptidase inhibitors: diversification utilizing a ROMP-derived coupling reagent", J Comb Chem. Mar.-Apr. 2008;10(2):195-203.
Wang et al., "Discovery of inhibitors of *Escherichia coli* methionine aminopeptidase with the Fe(II)—form selectivity and antibacterial activity", J Med Chem. Oct. 9, 2008;51(19):6110-20.
Wang et al. "Lead optimization of methionine aminopeptidase-2 (MetAP2) inhibitors containing sulfonamides of 5,6-disubstituted anthranilic acids", Bioorg Med Chem Lett. May15, 2007;17(10):2817-22. Epub Feb. 25, 2007.
Wang et al. "Tumor Suppression by a Rationally Designed Reversible Inhibitor of Methionine Aminopeptidase-2", Cancer Res. 63:7861-7869, 2003.
Weinsier et al., "Gallstone Formation and Weight Loss," Obes Res.,1(1):51-56 (1993).
Weinsier et al., "Medically Safe Rate of Weight Loss for the Treatment of Obesity: A Guideline Based on Risk of Gallstone Formation," Am. J. Med. 98(2):115-117 (1995).
Winter et al., "Endothelial αvβ3 Integrin—Targeted Fumagillin Nanoparticles Inhibit Angiogenesis in Atherosclerosis," Arterioscler. Thromb. Vasc. Biol., 26(9):2103-2109 (2006).
Written Opinion for International Application No. PCT/US2009/066816, mailed Apr. 8, 2010, 3 pages.
Written Opinion for International Application No. PCT/US2011/060127, mailed May 10, 2013, 4 pages.
Written Opinion for International Application No. PCT/US2011/062320, mailed May 29, 2013, 5 pages.
Yanai et al., "Antitumor Effect of Arterial Administration of a Medium-Chain Triglyceride Solutionof an Angiogenesis Inhibitor, TNP-470, in Rabbits Bearing VX-2 Carcinoma," Pharm Res. ,12(5):653-657 (May 1995).
Yanai et al., "Antitumor Activity of a Medium-Chain Triglyceride Solution of the Angiogenesis Inhibitor TNP-470 (AGM-1470) when Administered Via the Hepatic Artery to Rats Bearing Walker 256 Carcinosarcoma in the Liver," J. Pharmacol. Exp. Ther., 271(3):1267-1273 (Dec. 1994).
Zhang et al., "Angiogenesis inhibitors specific for methionine aminopeptidase 2 as drugs for malaria and leishmaniasis," J. Biomed. Sci., 9(1):34-40 (Jan.-Feb. 2002).
European Communication for EP Application No. 12 798 444.1, dated Aug. 28, 2015 (8 pages).
U.S. Appl. No. 14/856,929, Treatment of Obesity Using Non-Daily Administration of 6-O(4-Dimethylaminoethyoxy) Cinnamoyl Fumafillol, Sep. 17, 2015.

METHODS OF TREATING AGE RELATED DISORDERS

CROSS REFERENCE TO RELATED APPLICATIONS

This application is a continuation of International Application No. PCT/US2012/000461 filed Oct. 3, 2012 which claims priority to U.S. Provisional Patent Application 61/542,393 filed Oct. 3, 2011, each of these prior applications is incorporated by reference in its entirety.

BACKGROUND

Decreased mitochondrial function and increased oxidative damage has been linked to range of pathologic conditions associated with aging pathology, and it is commonly understood that oxidative damage participates in the functional deterioration of aging. For example, it appears that mitochondrial oxidative damage accumulates, and mitochondrial function declines, with chronological age. Further, mitochondrial reactive oxygen species production and global oxidative damage to protein, DNA and lipids increases with chronological age.

Oxidative stress caused by an imbalance between the production and detoxification of reactive oxygen species, such as peroxides and free radicals, has been implicated in a variety of pathological and chronic degenerative conditions including cancer, diabetes mellitus, arthritis, neurodegenerative disorders such as dementia, Alzheimer' disease, Parkinson's disease, and Hungtinton's disease, as well as age-related decline in cognitive function, cardiopulmonary function, muscle strength, vision, and hearing.

There are several sources by which reactive oxygen species are generated. However, the most important source of reactive oxygen species is probably the leakage of activated oxygen from mitochondria during normal oxidative respiration and energy production. Studies of the various components of mitochondria have provided tremendous insight into the role of mitochondria in oxidative stress. For example, molecular and genetic studies of MCLK1 (also known as CLK-1 and COQ7), a mitochondrial enzyme necessary for ubiquinone biosynthesis, indicate that a reduction of MCLK1 expression increased mitochondria oxidative stress, but also led to an overall decrease in non-mitochondrial oxidative damage accompanied by a decrease in systemic biomarkers of oxidative stress and aging (Lapointe et al., (2008), *The Journal of Biochemistry* 283 (38): 26217-26227; Lapointe et al., (2010) *Cell. Mol. Life Sci.* 67: 1-8). Partial inactivation of MCLK1 also prolonged the lifespan of nematodes and mice. Together, these studies suggest a link between mitochondrial energy metabolism, oxidative damage, and the aging process. Oxidative stress acts in an integrated manner to increase susceptibility to diseases generally considered to be related to the process of biological aging, including diabetes, peripheral vascular disease, uremia, ischemic stroke, and cataracts, as well as for both cardiovascular and noncardiovascular mortality in the elderly. (Kushner (2001), *Cleveland Clinic Journal of Medicine* 68:535-537).

There remains a dramatic need for new methods of preventing and/or treating the various pathological and chronic degenerative disorders associated with aging, e.g., associated with oxidative stress.

SUMMARY

Provided herein is a method of treating an oxidative stress disorder, such as Alzheimer's disease or an age-related disorder (e.g., osteoarthritis, sarcopenia and/or frailty) in a patient in need thereof, comprising administering to said patient an therapeutically effective amount of a MetAP2 inhibitor.

Also provided herein is a method of treating memory impairment, for example, memory impairment due to Alzheimer's disease, senile dementia, mild cognitive impairment due to aging, schizophrenia, Parkinson's disease, Huntington's disease, Pick's disease, Creutzfeldt-Jakob disease, depression, aging, stroke, CNS hypoxia, cerebral senility, cardiovascular disease, head trauma or age-related cognitive decline, in a patient in need thereof comprising administering to said patient an therapeutically effective amount of a MetAP2 inhibitor.

A method of enhancing cognitive function in a patient is contemplated herein, comprising administering to said patient an effective amount of a MetAP2 inhibitor. Also contemplated herein is a method of treating an age-related disorder (e.g., type 2 diabetes, Alzheimer's disease, osteoarthritis, senile dementia, and premature death) in a patient in need thereof, comprising administering an effective amount of a MetAP2 inhibitor compound to the patient, and wherein said compound, upon administration increases the level of metabolic products formed in the citric acid cycle and does not substantially increase alphaketoglutarate in the liver of said patient.

In some embodiments, a patient treated by a disclosed method exhibits a reduction in expression of mCLK1, exhibits a decrease in non-mitochondrial oxidative damage, and/or exhibits increased mitochondrial oxidative stress.

A method of decreasing the rate of development of one or more markers indicative of aging (e.g., an oxidative biomarker, e.g., a C-reactive protein) in a patient in need thereof, is provided, comprising administering to said patient a therapeutically effective amount of a MetAP2 inhibitor.

DETAILED DESCRIPTION

Overview

Figure 1:
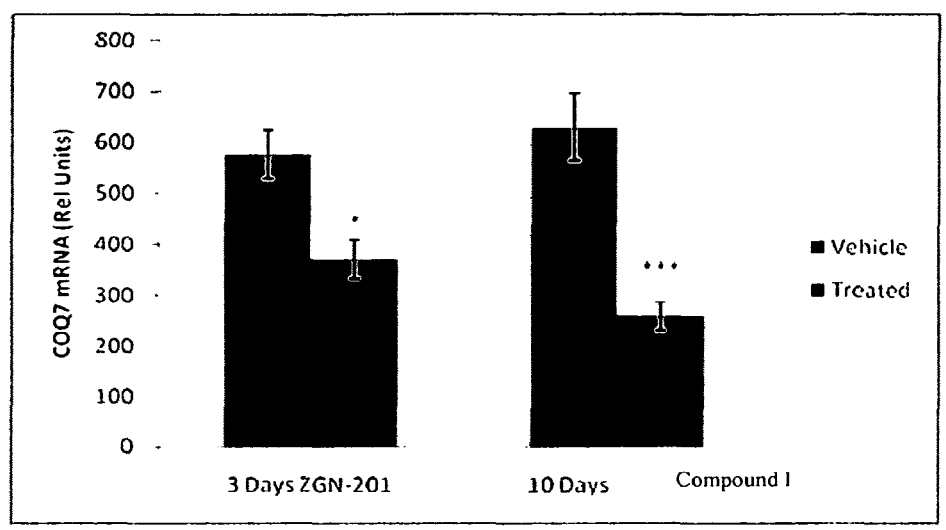
FIG. 1 depicts hepatic MCLK1 mRNA levels after treatment with MetAP2 inhibitors.

The disclosure relates at least in part to methods for treating a patient suffering from oxidative distress disorders including age-related disorders. For example, provided herein are methods of treating Alzheimer's disease, type 2 diabetes, congestive heart failure, osteoarthritis, sarcopenia, frailty, senile dementia, and premature death. The disclosure also relates in part to methods of enhancing cognitive function and treating memory impairment associated with Alzheimer's disease, senile dementia, schizophrenia, Parkinson's disease, Huntington's disease, Pick's disease, Creutzfeldt-Jakob disease, depression, aging, stroke, central nervous system (CNS) hypoxia, cerebral senility, cardiovascular disease, head trauma, and/or age-related cognitive decline. The disclosed methods are contemplated to prevent and/or treat a patient affected by the aforementioned disorders, which include administering an effective amount of a methionine aminopeptidase 2 (MetAP2) inhibitor.

MetAP2 encodes a protein that functions at least in part by enzymatically removing the amino terminal methionine residue from certain newly translated proteins. Increased expression of the MetAP2 gene has been historically associated with various forms of cancer. Molecules inhibiting the enzymatic activity of MetAP2 have been identified and have been explored for their utility in the treatment of various tumor types and infectious diseases such as microsporidiosis, leishmaniasis, and malaria.

As disclosed herein, MetAP2 inhibitors can effectively reduce the expression of MCLK1, a mitochondrial enzyme involved in the synthesis of ubiquinone, a membrane antioxidant and essential electron transporter of the mitochondrial respiratory chain. MCLK1 has also been implicated in the control of lifespan in nematodes and in mice. Without being limited by any particular theory or mechanism of action, it is believed that administration of a MetAP2 inhibitor suppresses the expression of MCLK1, that can result in a slower rate of mitochondrial electron transport, and consequently lower ATP and NAD(H) production. Such lowered ATP and NAD(H) levels can lead to an overall decrease in non-mitochondrial (e.g., cytoplasmic) oxidative damage and/or can reduce the overall reactive oxygen species damage associated with aging as exemplified by, for example, a reduction in age-associated systemic biomarkers of oxidative stress.

In an embodiment, long-term treatment (e.g. 4 weeks, 6 months, 1 year or more, e.g. about 1 month to about 1 year treatment duration) with MetAP2 inhibitors effectively and/or substantially prevents deterioration of neuromuscular coordination and function in a patient, e.g. a older patient (e.g. a patient over 50 years old, e.g. 45 years old to about 90 or 100 years old). For example, such prevention of deterioration can be for example, measured using the Rotarod test, a standard test of coordination that assesses the ability of an aging animal to remain balanced on a rotating beam. Without being limited by any particular theory or mechanistic links, it is believed that administration of a MetAP2 inhibitor reduces the decline in function of the neuromuscular and skeletal system, that can result in improved balance, neurological function, and resistance to decline in motor function and skills that normally occur with aging and that predispose individuals to decline in health and well-being.

Accordingly, disclosed herein are methods of treating age-related disorders using MetAP2 inhibitors; e.g. MetAP2 may be used in some embodiments to prevent and/or treat subjects with, or at risk of, oxidative distress disorders including age-related disorders. Disclosed herein are methods relating to administering a MetAP-2 inhibitor to treat oxidative distress disorders and/or age-related disorders, e.g., by administering an effective amount of a MetAP-2 inhibitor, e.g. a therapeutically effective amount that reduces expression of MCLK1 in a patient. Also disclosed herein are methods relating to administering a MetAP-2 inhibitor to treat memory impairment and to enhance the cognitive, metabolic and/or neuromuscular function of a patient in need thereof. In certain embodiments, upon administration of the MetAP2 inhibitor, a patient may exhibit a decrease in non-mitochondrial oxidative damage. In some embodiments, disclosed therapeutically effective amounts of MetAP2 inhibitors may not substantially modulate or suppress angiogenesis.

Also disclosed herein are methods of determining the need of individual patients for MetAP2 inhibitor treatment comprising measuring the plasma concentrations of C-reactive protein in the patient, administering a disclosed MetAP2 inhibitor based on an elevated basal level (e.g. a level of above 2.4 mg/L, or above 10 mg/L) of C-reactive protein, and/or determining the extent and/or duration of benefit derived from MetAP2 inhibitor therapy, e.g. by assessing the impact on circulating C-reactive protein concentrations in plasma or other biological samples.

Disclosed methods may include continuing administration of a MetAP2 inhibitor until a return to a normal range of a marker level (e.g., a C-reactive protein level, e.g. a C-reactive protein level between about 0.1 mg/L to about 10 mg/L) or to a desired change in clinical symptom.

MetAP2 Inhibitors

MetAP2 inhibitors refer to a class of molecules that inhibit or modulate the activity of MetAP2, e.g., the ability of MetAP2 to cleave the N-terminal methionine residue of newly synthesized proteins to produce the active form of the protein, or the ability of MetAP2 to regulate protein synthesis by protecting the subunit of eukaryotic initiation factor-2 (eIF2) and/or ERK1/2 from phosphorylation. MetAP2 inhibitors provided herein may be reversible or irreversible inhibitors.

Exemplary MetAP2 inhibitors may include irreversible inhibitors that covalently bind to MetAP2. For example, such irreversible inhibitors include fumagillin, fumagillol, and fumagillin ketone.

Derivatives and analogs of fumagillin, and pharmaceutically acceptable salts thereof are contemplated herein as irreversible MetAP2 inhibitors, such as O-(4-dimethylaminoethoxycinnamoyl)fumagillol (also referred to herein as Compound A or ZGN-433), O-(3,4,5-trimethoxycinnamoyl)fumagillol, O-(4-chlorocinnamoyl)fumagillol; O-(4-aminocinnamoyl)fumagillol; O-(4-dimethylaminoethoxycinnamoyl)fumagillol; O-(4-methoxycinnamoyl)fumagillol; O-(4-dimethylaminocinnamoyl)fumagillol; O-(4-hydroxycinnamoyl)fumagillol; O-(3,4-dimethoxycinnamoyl)fumagillol; O-(3,4-methylenedioxycinnamoyl)fumagillol; O-(3,4,5-trimethoxycinnamoyl)fumagillol; O-(4-nitrocinnamoyl)fumagillol; O-(3,4-dimethoxy-6-aminocinnamoyl)fumagillol; O-(4-acetoxy-3,5-dimethoxycinnamoyl)fumagillol; O-(4-ethylaminocinnamoyl)fumagillol; O-(4-ethylaminoethoxycinnamoyl)fumagillol; O-(3-di methylaminomethyl-4-methoxycinnamoyl)fumagillol; O-(4-trifluoromethylcinnamoyl)fumagillol; O-(3,4-dimethoxy-6-nitrocinnamoyl)fumagillol; O-(4-acetoxycinnamoyl)fumagillol; O-(4-cyanocinnamoyl)fumagillol; 4-(4-methoxycinnamoyl)oxy-2-(1,2-epoxy-1,5-dimethyl-4-hexenyl)-3-methoxy-1-chloromethyl-1-cyclohexanol; O-(3,4,5-trimethoxycinnamoyl)fumagillol; O-(4-dimethylaminocinnamoyl)fumagillol; O-(3,4,5-trimethoxycinnamoyl)oxy-2-(1,2-epoxy-1,5-dimethyl-4-hexenyl)-3-m-ethoxy-1-chloromethyl-1-cyclohexanol; O-(4-dimethylaminocinnamoyl)oxy-2-(1,2-epoxy-1,5-dimethyl-4-hexenyl)-3-me-thoxy-1-chloromethyl-1-cyclohexanol; O-(3,5-dimethoxy-4-hydroxycinnamoyl)fumagillol or O-(chloracetyl-carbamoyl) fumagillol(TNP-470), and/or pharmaceutically acceptable salts thereof (e.g. O-(4-dimethylaminoethoxycinnamoyl)fumagillol oxalate).

Fumagillin, and some derivatives thereof, have a carboxylic acid moiety and can be administered in the form of the free acid. Alternatively, contemplated herein are pharmaceutically acceptable salts of fumagillin, fumagillol, and derivatives thereof.

Pharmaceutically acceptable salts illustratively include those that can be made using the following bases: ammonia, L-arginine, benethamine, benzathene, betaine, bismuth, calcium hydroxide, choline, deanol, diethanolamine, diethylamine, 2-(diethylamino)ethanol, ethylenediamine, N-methylglucamine, hydrabamine, 1H-imidazole, lysine, magnesium hydroxide, 4-(2-hydroxyethyl)morpholine, piperazine, potassium hydroxide, 1-(2-hydroxyethyl)pyrrolidine, sodium hydroxide, triethanolamine, zinc hydroxide, dicyclohexlamine, or any other electron pair donor (as described in Handbook of Pharmaceutical Salts, Stan & Wermuth, VHCA and Wiley, Uchsenfurt-Hohestadt Germany, 2002). Contemplated pharmaceutically acceptable salts may include hydrochloric acid, bromic acid, sulfuric acid, phosphoric acid, nitric acid, formic acid, acetic acid, trifluoroacetic acid, oxalic acid, fumaric acid, tartaric acid, maleic acid, methanesulfonic acid, benzenesulfonic acid or para-toluenesulfonic acid.

Esters of the present invention may be prepared by reacting fumagillin or fumagillol with the appropriate acid under standard esterification conditions described in the literature (Houben-Weyl 4th Ed. 1952, Methods of Organic Synthesis). Suitable fumagillin esters include ethyl methanoate, ethyl ethanoate, ethyl propanoate, propyl methanoate, propyl ethanoate, and methyl butanoate.

In another embodiment, contemplated irreversible inhibitors of MetAP2 may include a siRNA, shRNA, an antibody or an antisense compound of MetAP2.

Further examples of reversible and irreversible MetAP2 inhibitors are provided in the following references, each of which is hereby incorporated by reference: Olson et al. (U.S. Pat. No. 7,084,108 and WO 2002/042295), Olson et al. (U.S. Pat. No. 6,548,477; U.S. Pat. No. 7,037,890; U.S. Pat. No. 7,084,108; U.S. Pat. No. 7,268,111; and WO 2002/042295), Olson et al. (WO 2005/066197), Hong et al. (U.S. Pat. No. 6,040,337)., Hong et al. (U.S. Pat. No. 6,063,812 and WO 1999/059986), Lee et al. (WO 2006/080591), Kishimoto et at (U.S. Pat. No. 5,166,172; U.S. Pat. No. 5,698,586; U.S. Pat. No. 5,164,410; and 5,180,738), Kishimoto et al. (U.S. Pat. No. 5,180,735), Kishimoto et al. (U.S. Pat. No. 5,288,722), Kishimoto et al. (U.S. Pat. No. 5,204,345), Kishimoto et al. (U.S. Pat. No. 5,422,363), Liu et al. (U.S. Pat. No. 6,207,704; U.S. Pat. No. 6,566,541; and WO 1998/056372), Craig et al. (WO 1999/057097), Craig et al. (U.S. Pat. No. 6,242,494), BaMaung et al. (U.S. Pat. No. 7,030,262), Comess et al. (WO 2004/033419), Comess et al. (US 2004/0157836), Comess et al. (US 2004/0167128), Henkin et al. (WO 2002/083065), Craig et al. (U.S. Pat. No. 6,887,863), Craig et al. (US 2002/0002152), Sheppard et al. (2004, Bioorganic & Medicinal Chemistry Letters 14:865-868), Wang et al. (2003, Cancer Research 63:7861-7869), Wang et al. (2007, Bioorganic & Medicinal Chemistry Letters 17:2817-2822), Kawai et al. (2006, Bioorganic & Medicinal Chemistry Letters 16:3574-3577), Henkin et al. (WO 2002/026782), Nan et al. (US 2005/0113420), Luo et al. (2003, J. Med. Chem., 46:2632-2640), Vedantham et al. (2008, J. Comb. Chem., 10:195-203), Wang et al. (2008, J. Med. Chem., 51:6110-20), Ma et al. (2007, BMC Structural Biology, 7:84) and Huang et al. (2007, J. Med. Chem., 50:5735-5742), Evdokimov et al. (2007, PROTEINS: Structure, Function, and Bioinformatics, 66:538-546), Garrabrant et al. (2004, Angiogenesis 7:91-96), Kim et al. (2004, Cancer Research, 64:2984-2987), Towbin et al. (2003, The Journal of Biological Chemistry, 278(52):52964-52971), Marino Jr. (U.S. Pat. No. 7,304,082), Kallender et al. (U.S. patent application number 2004/0192914), and Kallender et al. (U.S. patent application numbers 2003/0220371 and 2005/0004116).

For example, contemplated MetAP2 inhibitors may include:

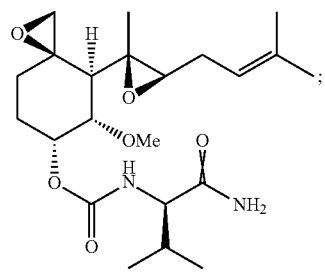

(B)

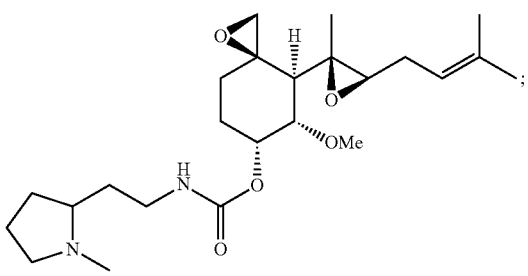

(C)

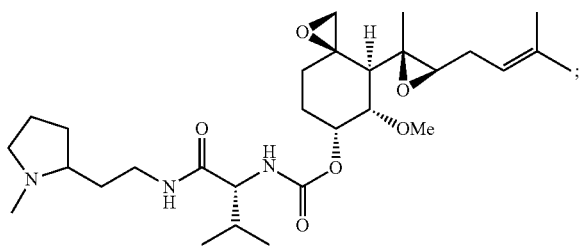

(D)

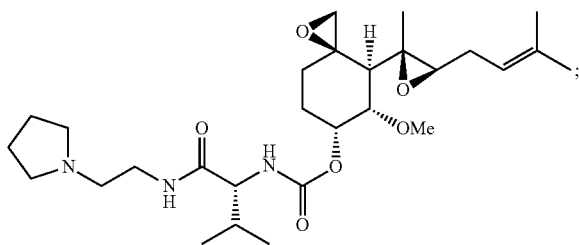

(E)

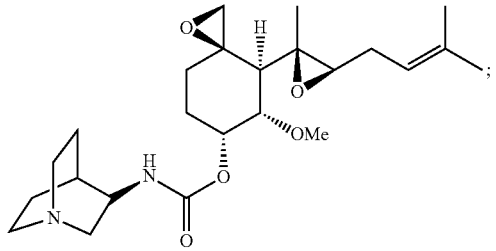

(F)

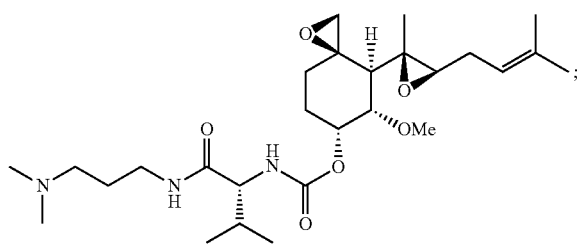

(G)

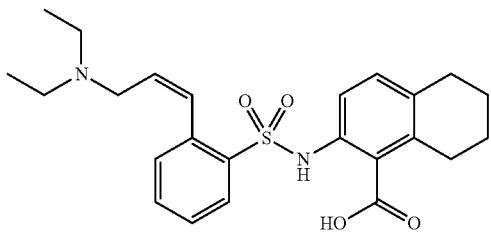

(H)

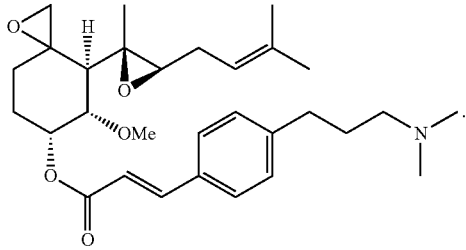

(I)

In some embodiments, a contemplated MetAP2 inhibitor may modulate MCLK1. For example, a disclosed MetAP2 inhibitor may decrease the mRNA levels or protein levels of MCLK1 in a subject after administration, e.g., after 1, 3, 5, and/or 10 days or more of treatment.

In an embodiment, a contemplated MetAP2 inhibitor may decrease non-mitochondrial oxidative damage in a patient. In another embodiment, a contemplated MetAP2 inhibitor may decrease the rate of development of one or more markers indicative of aging in a patient. In yet another embodiment, a contemplated MetAP2 inhibitor may increase mitochondrial oxidative stress in a patient. In a further embodiment, a contemplated MetAP2 inhibitor increases the levels of citric acid cycle metabolites in a patient without increasing alphaketoglutarate.

Methods

A method of treating, and/or mitigating or minimizing the risk of, oxidative distress disorders in a patient in need thereof is provided herein, comprising parenterally or non-parenterally administering a therapeutically effective amount of a MetAP2 inhibitor to said patient. In one embodiment, the instant disclosure embraces a method of treating an oxidative stress disorder selected from an age-related disorder, a neurodegenerative disorder, a mitochondrial disorder, and an impaired energy processing disorder.

For example, contemplated methods include treatment of age-related disorders, including, but not limited to, macular degeneration, diabetes mellitus, osteoarthritis, rheumatoid arthritis, sarcopenia, cardiovascular diseases such as hypertension, atherosclerosis, coronary artery disease, ischemia/reperfusion injury, cancer, premature death, as well as age-related decline in cognitive function, cardiopulmonary function, muscle strength, vision, and hearing. Contemplated methods also include treatment of a neurodegenerative disorder or neurological disease, including, but not limited to, Motor Neuron Disease, Creutzfeldt-Jakob disease, Machado-Joseph disease, Spino-cerebellar ataxia, Multiple sclerosis (MS), Parkinson's disease, Alzheimer's disease, Huntington's disease, hearing and balance impairments, ataxias, epilepsy, mood disorders such as schizophrenia, bipolar disorder, and depression, dementia, Pick's Disease, stroke, CNS hypoxia, cerebral senility, and neural injury such as head trauma. Contemplated methods further include treatment of a mitochondrial disorder, including, but not limited to, Myoclonic Epilepsy with Ragged Red Fibers (MERRF), Mitochondrial Encephalomyopathy, Lactic acidosis, and Stroke-like episodes (MELAS), Maternally Inherited Diabetes and Deafness (MIDD), Leber's Hereditary Optic Neuropathy (LHON), chronic progressive external ophthalmoplegia (CPEO), Leigh Disease, Kearns-Sayre Syndrome (KSS), Friedreich's Ataxia (FRDA), Co-Enzyme Q10 (CoQ10) deficiency, Complex I Deficiency, Complex II Deficiency, Complex III Deficiency, Complex IV Deficiency, Complex V Deficiency, myopathies (including cardiomyopathy and encephalomyopathy), and renal tubular acidosis. Additionally, contemplated methods include treatment of patients affected with an impaired energy processing disorder, including, but not limited to, haemaglobionopathies, thalassemia, sickle cell anemia, or energy impairment due to deprivation, poisoning or toxicity of oxygen.

Also provided herein are methods of treating memory impairment in a patient in need thereof, comprising parenterally or non-parenterally administering a therapeutically effective amount of a MetAP2 inhibitor to said patient. In another embodiment, provided herein are methods of enhancing cognitive function in a patient in need thereof, comprising parenterally or non-parenterally administering a therapeutically effective amount of a MetAP2 inhibitor to said patient. Such patients may suffer from memory impairment due to, for example, Alzheimer's disease, dementia (e.g., senile dementia), mild cognitive impairment due to aging, schizophrenia, Parkinson's disease, Huntington's disease, Pick's disease, Creutzfeldt-Jakob disease, depression, aging, stroke, CNS hypoxia, cerebral senility, cardiovascular disease, head trauma, or age-related cognitive decline.

In another embodiment, provided herein are methods of decreasing the rate of development of one or more biomarkers indicative of aging in a patient, comprising parenterally or non-parenterally administering a therapeutically effective amount of a MetAP2 inhibitor to said patient. In an embodiment, the one or more biomarkers indicative of aging is an energy or oxidative biomarker. Exemplary energy or oxidative biomarkers include, but are not limited to, lactic acid (lactate) levels, pyruvic acid (pyruvate) levels, lactate/pyruvate ratios, phosphocreatine levels, NADH or NADPH levels, NAD or NADP levels, ATP levels, reduced coenzyme Q levels, oxidized coenzyme Q levels, total coenzyme Q levels, oxidized cytochrome C levels, reduced cytochrome C levels, oxidized cytochrome C/reduced cytochrome C ratio, acetoacetate levels, beta-hydroxy butyrate levels, acetoacetate/beta-hydroxy butyrate ratio, 8-hydroxy-2'-deoxyguanosine (8-OHdG) levels, isoprostane levels, levels of reactive oxygen species, oxygen consumption ($VO_2$), carbon dioxide output ($VCO_2$), and respiratory quotient ($VCO_2/VO_2$). Biomarkers can be measured in whole blood, plasma, cerebrospinal fluid, cerebroventricular fluid, arterial blood, venous blood, or any other body fluid, body gas, or other biological sample useful for such measurement.

In some embodiments, administration of a contemplated therapeutically effective amount of a MetAP2 inhibitors results in a reduction in expression of MCLK1 in the patient. Such administration of MetAP2 inhibitors may also result in a decrease in non-mitochondrial oxidative damage. In another embodiment, such administration of MetAP2 inhibitors may result in an increase in mitochondrial oxidative stress. In yet a further embodiment, administration of a therapeutically effective amount of a MetAP2 inhibitors increases the level of metabolic products formed in the citric acid cycle but does not substantially increase the level of alphaketoglutarate in the liver of the treated patient. In another embodiment, methods of extending lifespan of a mammal are contemplated. For example, contemplated herein is a reduction (e.g. by 1%, 5% 30% or 50% of the expression of mCLK1 a patient, which may result in extended lifespan by as much as 1%, 5%, 20% or 30%.

In some embodiments, a contemplated therapeutically effective amount of a MetAP2 inhibitor, does not substantially modulate or suppress angiogenesis, but is still effective as a MetAP2 inhibitor. The term "angiogenesis" is known to persons skilled in the art, and refers to the process of new blood vessel formation, and is essential for the exponential growth of solid tumors and tumor metastasis.

It is understood that the administration of a MetAP2 inhibitor, for example, to treat an oxidative stress disorder, as described herein can be part of a combination therapy, for example, administered with (e.g. before, during, or after) administration of another active agent or treatment regimen such as chemotherapy treatment, and/or radiation treatment. It is contemplated that co-administration of a MetAP-2 inhibitor and another active agent can occur at the same time. In other embodiments, administration of a MetAP-2 inhibitor occurs immediately prior to or immediately after administration of another active agent. In yet another embodiment, a period of time may elapse between administration of a MetAP-2 inhibitor and another agent.

Administration and Formulation

Contemplated herein are formulations suitable for parenteral or non-parenteral administration of MetAP2 inhibitors. In certain embodiments, a subject may have a lower systemic exposure (e.g. at least about 2, 3, 5, 10, 20, or at least about 30% less systemic exposure) to the non-parenterally (e.g. orally) administered of a MetAP2 inhibitor as compared to a subject parenterally (e.g. subcutaneously) administered the same dose of the MetAP2 inhibitor.

Contemplated non-parenteral administration includes oral, buccal, transdermal (e.g. by a dermal patch), topical, inhalation, sublingual, ocular, pulmonary, nasal, or rectal administration.

Contemplated parenteral administration includes intravenous and subcutaneous administration, as well as administration at a site of a minimally-invasive procedure or a surgery.

In an embodiment, provided herein are effective dosages, e.g. a daily dosage of a MetAP2 inhibitor, that may not substantially modulate or suppress angiogenesis. For example, provided here are methods that include administering doses of MetAP2 inhibitors that are effective for e.g. reducing MCLK1 expression, but are significantly smaller doses than that necessary to modulate and/or suppress angiogenesis (which may typically require about 12.5 mg/kg to about 50 mg/kg or more). For example, contemplated dosage of a MetAP2 inhibitor in the methods described herein may include administering about 25 mg/day, about 10 mg/day, about 5 mg/day, about 3 mg/day, about 2 mg/day, about 1 mg/day, about 0.75 mg/day, about 0.5 mg/day, about 0.1 mg/day, about 0.05 mg/day, or about 0.01 mg/day.

For example, a therapeutically effective amount of the drug for administering to a patient in need thereof may be about 0.0001 mg/kg to about 25 mg/kg of body weight per day. For example, a contemplated dosage may from about 0.01 mg/kg to about 10 mg/kg of body weight per day, about 0.01 mg/kg to about 1 mg/kg of body weight per day, about 0.01 mg/kg to about 0.1 mg/kg of body weight per day, about 0.04 mg/kg to about 10 mg/kg of body weight per day, or about 0.04 to about 1 mg/kg of body weight per day. In an embodiment, a MetAP2 inhibitor such as disclosed herein (e.g. O-(4-dimethlyaminoethoxycinnamoyl)fumagillol), may be administered at about 0.04 to about 1 mg/kg of a patient.

Contemplated methods may include administration of a composition comprising a MetAP2 inhibitor, for example, hourly, twice hourly, every three to four hours, daily, twice daily, 1, 2, 3 or 4 times a week, every three to four days, every week, or once every two weeks depending on half-life and clearance rate of the particular composition or inhibitor.

Treatment can be continued for as long or as short a period as desired. The compositions may be administered on a regimen of, for example, one to four or more times per day. A suitable treatment period may be, for example, at least about one week, at least about two weeks, at least about one month, at least about six months, at least about 1 year, or indefinitely. A treatment regimen may include a corrective phase, during which a MetAP2 inhibitor dose sufficient to provide e.g., a reduction of MCLK1 expression, followed by a maintenance phase, during which a lower MetAP2 inhibitor dose sufficient to reduce or prevent increase in MCLK1 expression level is administered.

For pulmonary (e.g., intrabronchial) administration, MetAP2 inhibitors may be formulated with conventional excipients to prepare an inhalable composition in the form of a fine powder or atomizable liquid. For ocular administration, MetAP2 inhibitors may be formulated with conventional excipients, for example, in the form of eye drops or an ocular implant. Among excipients useful in eye drops are viscosifying or gelling agents, to minimize loss by lacrimation through improved retention in the eye.

Liquid dosage forms for oral or other administration include, but are not limited to, pharmaceutically acceptable emulsions, microemulsions, solutions, suspensions, syrups and elixirs. In addition to the active agent(s), the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the ocular, oral, or other systemically-delivered compositions can also include adjuvants such as wetting agents, and emulsifying and suspending agents.

Dosage forms for topical or transdermal administration of an inventive pharmaceutical composition may include ointments, pastes, creams, lotions, gels, powders, solutions, sprays, inhalants, or patches. The active agent is admixed under sterile conditions with a pharmaceutically acceptable carrier and any needed preservatives or buffers as may be required. For example, cutaneous routes of administration are achieved with aqueous drops, a mist, an emulsion, or a cream.

Transdermal patches may have the added advantage of providing controlled delivery of the active ingredients to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

When administered in lower doses, injectable preparations are also contemplated herein, for example, sterile injectable aqueous or oleaginous suspensions may be formulated according to the known art using suitable dispersing or wetting agents and suspending agents.

Compositions for rectal administration may be suppositories which can be prepared by mixing a MetAP2 inhibitor with suitable non-irritating excipients or carriers such as cocoa butter, polyethylene glycol or a suppository wax which are solid at ambient temperature but liquid at body temperature and therefore melt in the rectum and release the active agent(s). Alternatively, contemplated formulations can be administered by release from a lumen of an endoscope after the endoscope has been inserted into a rectum of a subject.

Oral dosage forms, such as capsules, tablets, pills, powders, and granules, may be prepared using any suitable process known to the art. For example, a MetAP2 inhibitor may be mixed with enteric materials and compressed into tablets.

Alternatively, formulations of the invention are incorporated into chewable tablets, crushable tablets, tablets that dissolve rapidly within the mouth, or mouth wash.

EXAMPLES

This example is not intended in any way to limit the scope of this invention but is provided to illustrate aspects of the disclosed methods. Many other embodiments of this invention will be apparent to one skilled in the art.

Example 1

Administration of MetAP2 Inhibitors Reduces Hepatic MCLK1 Levels in Mammals

C57BL/6 mice were treated for three days with orally administered fumigillin (ZGN-201) or for ten days with subcutaneously administered Compound 1. Liver mRNA levels of MCLK1 were then assessed by microarray analysis of samples obtained from four individual animals per treatment group (vehicle and fumagillin after three days of treatment, or vehicle and Compound 1 after 10 days of treatment), using the Illumina MouseRef8 chip system Analysis of background-subtracted data was conducted using the Illumina BeadStudio software according to manufacturer's specifications.

FIG. 1 depicts the hepatic MCLK1 mRNA levels in treated mice and indicates that MCLK1 levels were reduced by approximately 30-60% in the livers of mice treated with either compound. FIG. 1 further illustrates the utility in modulating MCLK1 levels regardless of whether the MetAP2 inhibitor is administered orally or parenterally.

Example 2

Figure 2:
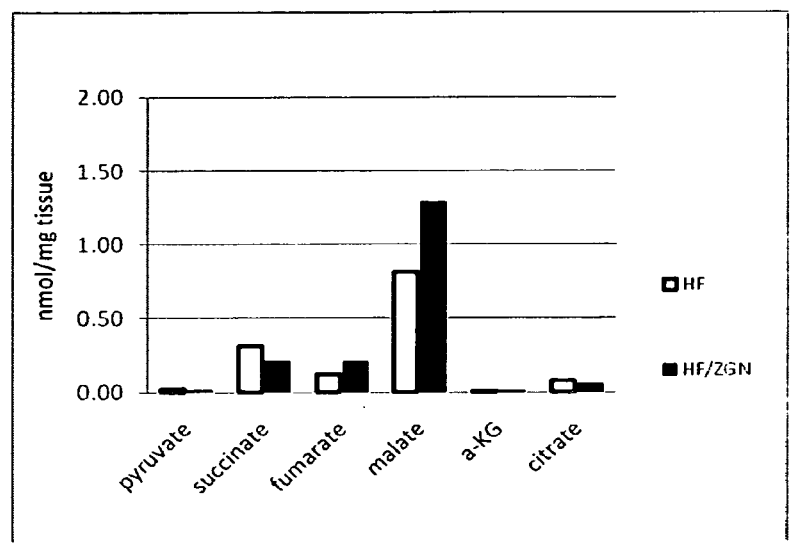
FIG. 2 indicates the effect of fumagillin treatment on the levels of citric acid cycle metabolites in rats.

Administration of MetAP2 Inhibitors Increases Citric Acid Cycle Metabolites in Mammals Male Wistar rats were fed a high fat diet (45% of calories) for 12 weeks to induce obesity, followed by an additional two weeks of continued exposure to diet containing either no drug (control) or fumagillin providing an average daily dose of 3 mg/kg of body weight. At 2 weeks, levels of metabolites known to participate in the citric acid cycle, such as pyruvate, succinate, fumarate, malate, and citrate, were measured in extracts of liver using liquid chromatography coupled with tandem mass spectrometry. In addition, the hepatic level of alphaketoglutarate (a-KG), the precursor of alphaketoglutarate dehydrogenase, was assessed in the same manner. FIG. 2 indicates that fumagillin treatment (ZGN) increased the levels of fumarate and malate in the livers of treated rats. However, fumagillin treatment did not alter the hepatic level of alphaketoglutarate.

An increase in expression and activity of the mitochondrial enzyme alphaketoglutarate dehydrogenase was also observed in the liver of similarly treated mCLK1 mutant mice.

Example 3

Administration of MetAP2 Inhibitors Improves Neuromuscular Coordination in Aging Mammals C57BL/6 mice were treated for 247 days with orally administered fumigillin (ZGN-201). Neuromuscular coordination was assessed using a standardized Rotarod test, which was repeated five times for each animal. Animals treated with ZGN-201 remained on the rotating rod for an average of 54.5 seconds, compared with 32.7 seconds for control animals.

Figure 3:
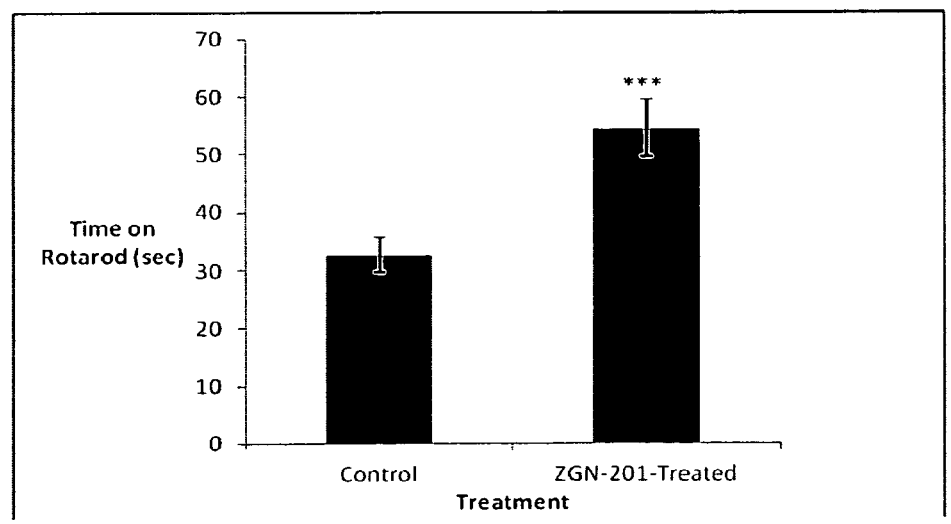
FIG. 3 depicts the results of neuromuscular coordination of mice after long time treatment with a MetAP2 inhibitor.

FIG. 3 depicts the results of the Rotarod test administered in mice treated with fumagillin (vs. control animals) for over eight months (roughly one half of the lifespan of the animals when fed this diet). FIG. 1 further illustrates the utility in preventing the decline in neuromuscular function that occurs with aging.

Example 4

Administration of MetAP2 Inhibitors Decreases Circulating C-Reactive Protein Concentrations in Humans Obese women were treated with a MetAP2 inhibitor (ZGN-433) by twice weekly intravenous administration. Before and after four weeks of treatment, levels of C-reactive protein were measured in plasma using a bead-based immunofluorescence assay.

Figure 4:
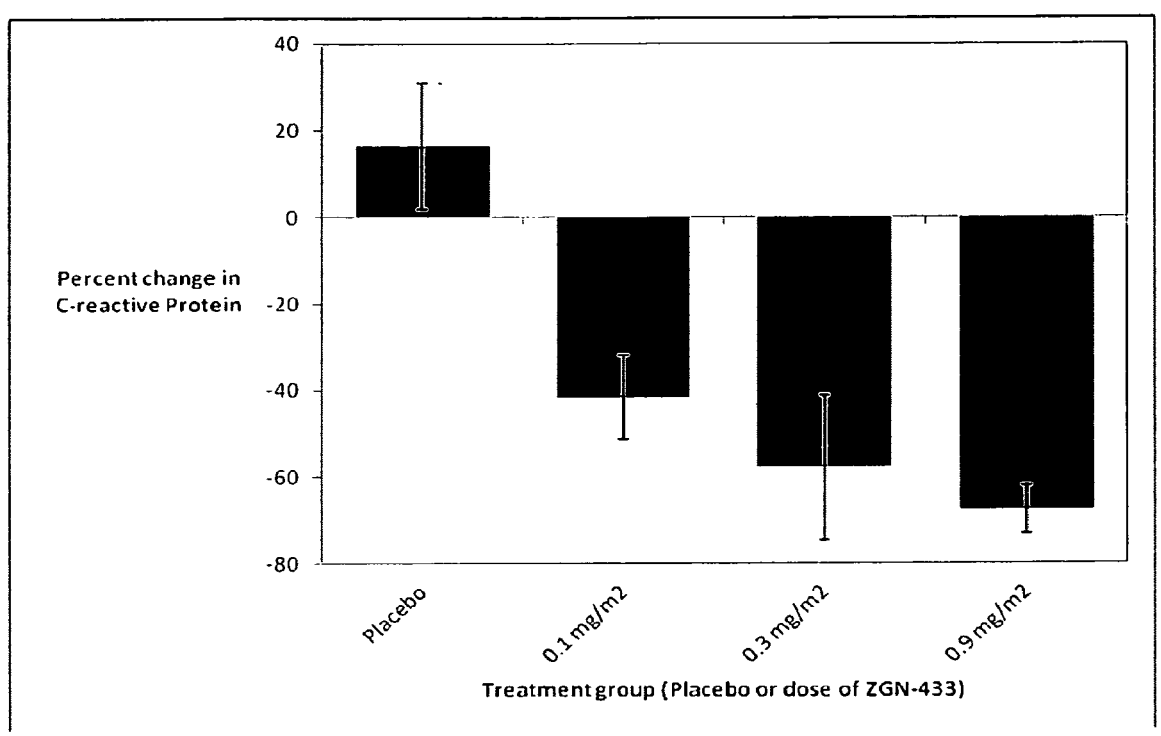
FIG. 4 depicts the decrease of C-reactive protein in patients after treatment with MetAP2.

FIG. 4 indicates that MetAP2 inhibitor treatment (ZGN) decreased the levels of C-reactive protein in the plasma.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

What is claimed is:

1. A method of treating an oxidative stress disorder in a patient in need thereof, comprising administering to said patient a therapeutically effective amount of a MetAP2 inhibitor selected from O-(4-dimethylaminoethoxycinnamoyl)fumagillol and pharmaceutically acceptable salts thereof, wherein the oxidative stress disorder is sarcopenia.

2. The method of claim 1, wherein said patient exhibits a reduction in expression of mCLK1.

3. The method of claim 1, wherein the patient, upon administration of the MetAP2 inhibitor, exhibits a decrease in non-mitochondrial oxidative damage.

4. The method of claim 1, wherein the patient, upon administration of the MetAP2 inhibitor, exhibits increased mitochondrial oxidative stress.

5. The method of claim 1, wherein said therapeutically effective amount does not substantially modulate or suppress angiogenesis.

6. The method of claim 1, further comprising administration of the MetAP2 inhibitor until a marker level is returned to a normal range.

7. The method of claim 6, wherein the marker is C-reactive protein.

8. The method of claim 1, wherein said MetAP2 inhibitor is administered parenterally or non-parenterally.

9. The method of claim 1, wherein the MetAP-2 inhibitor is administered at a dose of about 0.01 mg/kg to about 10 mg/kg.

10. The method of claim 1, wherein the MetAP-2 inhibitor is administered at a dose of about 0.04 mg/kg to about 1.0 mg/kg.

* * * * *